US012595223B2

(12) United States Patent
Billodeaux et al.

(10) Patent No.: US 12,595,223 B2
(45) Date of Patent: Apr. 7, 2026

(54) PROPIONIC ACID PROCESS

(71) Applicant: EASTMAN CHEMICAL COMPANY, Kingsport, TN (US)

(72) Inventors: Damon Ray Billodeaux, White Oak, TX (US); Kenneth Wayne Hampton, Jr., Kilgore, TX (US); Carey Dan Ashcroft, Longview, TX (US)

(73) Assignee: Eastman Chemical Company, Kingsport, TN (US)

( * ) Notice: Subject to any disclaimer, the term of this patent is extended or adjusted under 35 U.S.C. 154(b) by 447 days.

(21) Appl. No.: 18/019,147

(22) PCT Filed: Jul. 21, 2021

(86) PCT No.: PCT/US2021/042500
§ 371 (c)(1),
(2) Date: Feb. 1, 2023

(87) PCT Pub. No.: WO2022/031436
PCT Pub. Date: Feb. 10, 2022

(65) Prior Publication Data
US 2024/0002324 A1 Jan. 4, 2024

Related U.S. Application Data

(60) Provisional application No. 63/060,711, filed on Aug. 4, 2020.

(51) Int. Cl.
*C07C 51/09* (2006.01)
*B01J 31/20* (2006.01)
(Continued)

(52) U.S. Cl.
CPC .............. *C07C 51/09* (2013.01); *B01J 31/20* (2013.01); *B01J 31/2226* (2013.01);
(Continued)

(58) Field of Classification Search
CPC ....... C07C 67/38; C07C 51/09; C07C 53/122; C07C 69/24; B01J 31/2226
See application file for complete search history.

(56) References Cited

U.S. PATENT DOCUMENTS 3,944,604 A * 3/1976 Hershman ............ B01J 31/0231
502/169
3,989,747 A * 11/1976 Craddock ............... C07C 51/14
502/169

(Continued)

FOREIGN PATENT DOCUMENTS

GB 2 327 420 A 1/1999
WO WO 2001/051447 A2 7/2001
WO WO 2015/51447 * 7/2001 ............ C07C 51/12

OTHER PUBLICATIONS

Notification of Transmittal of the International Search Report and the Written Opinion of the International Searching Authority, or the Declarations date of mailing Nov. 3, 2021 received in International Application No. PCT/US2021/042500.

(Continued)

*Primary Examiner* — Yate' K Cutliff
(74) *Attorney, Agent, or Firm* — Steven A. Owen

(57) ABSTRACT

Provided is a one-pot process for preparing propionic acid, which comprises (i) treating ethylene with a $C_1$-$C_6$ alkanol, water, and carbon monoxide in the presence of a catalyst system comprising the reaction product of (a) a Group 8 to 10 transition metal compound such as a palladium or ruthenium compound; and (b) an activating anion, at elevated temperature and pressure. The process also provides a facile, continuous process for the preparation of propionic acid via the alkoxycarbonylation of ethylene at elevated temperature and pressure followed by hydrolysis, in one reaction vessel.

16 Claims, 1 Drawing Sheet

(51) Int. Cl.
  B01J 31/22 (2006.01)
  B01J 31/24 (2006.01)
  C07C 67/38 (2006.01)

(52) U.S. Cl.
  CPC ........... B01J 31/2409 (2013.01); C07C 67/38 (2013.01); B01J 2231/321 (2013.01); B01J 2531/004 (2013.01); B01J 2531/821 (2013.01); B01J 2531/824 (2013.01)

(56) References Cited

U.S. PATENT DOCUMENTS

| | | | |
|---|---|---|---|
| 4,148,830 | A | 4/1979 | Pruett et al. |
| 4,593,127 | A | 6/1986 | Bunning et al. |
| 4,717,775 | A | 1/1988 | Billig et al. |
| 4,769,498 | A | 9/1988 | Billig et al. |
| 6,348,621 | B1 | 2/2002 | Wang et al. |
| 6,476,255 | B1 | 11/2002 | Hadden et al. |
| 7,485,739 | B2 | 2/2009 | Eastham et al. |
| 2001/0051745 | A1 | 12/2001 | Pearson et al. |
| 2020/0392062 | A1* | 12/2020 | Kucmierczyk ......... C07C 51/09 |

OTHER PUBLICATIONS

Nobbs et al., "Isomerizing Methoxycarbonylation of Alkenes to Esters Using a Bis(phosphorinone)xylene Palladium Catalyst", American Chemical Society, Organometallics, 2017, 36, pp. 391-398.

Du Plessis et al., "Parameters Influencing Reactivity and Regioselectivity in the Methoxycarbonylation of Arylalkenes", Synthesis, 2016, 48, pp. 557-565.

Roesle et al., "A Comprehensive Mechanistic Picture of the Isomerizing Alkoxycarbonylation of Plant Oils", Journal of the American Chemical Society, 2014, 136, pp. 1687-16881.

Tshabalala et al., "Palladium complexes of (benzoimidazol-2-ylmethyl)amine ligands as catalysts for methoxycarbonylation of olefins", Journal of Molecular Catalysis A: Chemical, 406 (2015), pp. 178-184.

* cited by examiner

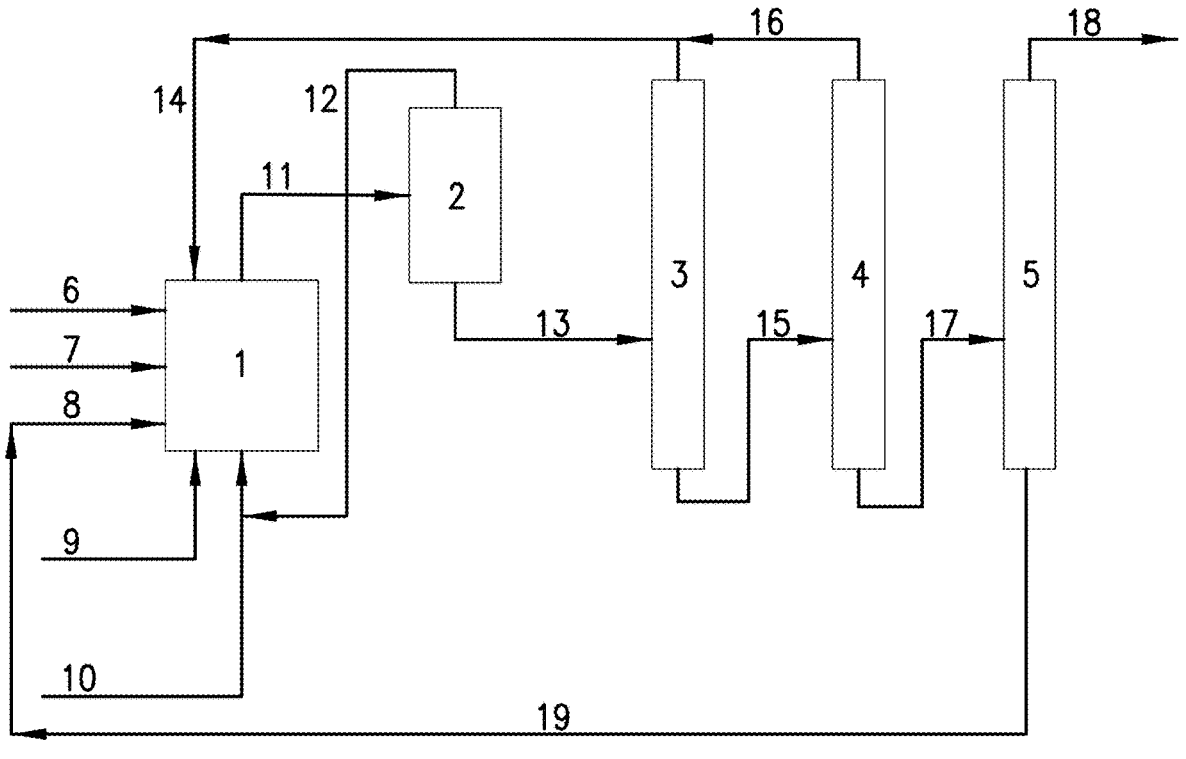

PROPIONIC ACID PROCESS

CROSS-REFERENCE TO RELATED APPLICATION(S)

This application is a national stage filing under 35 USC § 371 of International Application Number PCT/US2021/042500, filed on, Jul. 21, 2021 which claims the benefit of the filing date to U.S. Provisional Application No. 63/060,711, filed on Aug. 4, 2020, the entire disclosures of which are incorporated by reference herein.

FIELD OF THE INVENTION

This invention belongs to the field of synthetic organic chemistry. In particular, it relates to a one pot process for the alkoxylation of ethylene and subsequent hydrolysis to provide propionic acid.

BACKGROUND OF THE INVENTION

Propionic acid is produced from ethylene by the traditional hydroformylation process, with hydrogen and carbon monoxide, to give propionaldehyde, followed by air oxidation to give propionic acid. Hydrogen gas can be expensive to produce and typically requires an off-take from a nearby hydrocarbon cracker. In addition, oxidation of propionaldehyde to give propionic acid results in the production of unwanted byproducts, most notably acetic acid.

SUMMARY OF THE INVENTION

The invention is as set forth in the appended claims. In general, the invention provides a one-pot alkoxycarbonylation/hydrolysis process for preparing propionic acid, which comprises (i) treating ethylene with a $C_1$-$C_6$ alkanol, water, and carbon monoxide in the presence of a catalyst system comprising the reaction product of (a) a Group 8 to 10 transition metal compound such as a palladium or ruthenium compound; and (b) an activating anion, at elevated temperature and pressure. In the case of a catalyst system comprising a palladium compound, a phosphorous compound capable of forming a bidentate ligand is also necessary. The invention provides a facile, continuous process for the preparation of propionic acid via the alkoxycarbonylation of ethylene at elevated temperature and pressure and hydrolysis to provide propionic acid, in one reaction vessel.

BRIEF DESCRIPTION OF THE DRAWINGS

The FIGURE is a flow diagram of the process of the invention.

DETAILED DESCRIPTION OF THE INVENTION

The present invention provides one-pot process for preparing propionic acid, which comprises:
    (i) treating ethylene with a $C_1$-$C_6$ alkanol, water, and carbon monoxide in the presence of a catalyst system comprising the reaction product of:
    (a) a Group 8 to 10 transition metal compound; and
    (b) an activating anion;
at a temperature of about 50° C. to about 200° C., and a pressure of at least about 1375 kPa; provided that when said transition metal compound is palladium, the catalyst system further comprises at least one phosphorous compound.

As used herein, the singular forms "a", "an", and "the" include their plural referents unless the context clearly dictates otherwise. The terms "containing" or "including" are intended to be synonymous with the term "comprising", meaning that at least the named compound, element, particle, or method step, etc., is present in the composition or article but does not exclude the presence of other compounds, materials, method steps, etc., even if the other such compounds, material, particles, method steps, etc., have the same function as what is named, unless expressly excluded in the claims.

As used herein, the phrase "reaction product of" is used in recognition that while the catalyst system is described as having certain components, such starting materials may very well interact in solution; for example, the phosphorous compound may form a bidentate ligand with the transition metal, such as palladium. Similarly, the activating anion may be coordinated by other molecules in the catalyst system or may exist in solution unassociated with the other molecules.

In the present invention, the alkoxycarbonylation reaction of ethylene is carried out utilizing a homogeneous catalyst, i.e., a catalyst that is dissolved in the liquids contained within the reactor. The homogeneous catalyst system is comprised of a Group 8 to 10 transition metal compound in combination with or comprising an activating anion. In certain embodiments, the transition metal compound is chosen from iron, ruthenium, osmium, cobalt, nickel, palladium, rhodium, and platinum, combined with an activating anion. In one embodiment, the transition metal compound is chosen from compounds which contain at least one atom from ruthenium and palladium. In the case of palladium, the palladium compound is generally a salt of Pd(II) and in such cases, requires the presence of a phosphorous compound as described below. In the case of a ruthenium compound, the compound is generally introduced into the reactor as a Ruthenium(0) species, such as $Ru_3(CO)_{12}$.

In the case of palladium, suitable compounds of palladium include salts of palladium with, or compounds comprising weakly coordinated anions derived from, nitric acid; sulphuric acid; lower alkanoic (up to $C_{12}$) acids such as acetic acid and propionic acid including halogenated carboxylic acids such as trifluoroacetic acid and trichloroacetic acid; sulfonic acids such as methanesulfonic acid, chlorosulfonic acid, fluorosulfonic acid, trifluoromethanesulfonic acid, benzenesulfonic acid, naphthalene sulfonic acid, toluenesulfonic acids, e.g. p-toluenesulfonic acid, t-butylsulfonic acid, and 2-hydroxypropanesulfonic acid; sulfonated ion exchange resins; perhalic acids such as perchloric acid; halogenated carboxylic acids such as trichloroacetic acid and trifluoroacetic acid; orthophosphoric acid; phosphonic acids such as benzenephosphonic acid; and acids derived from interactions between Lewis acids and Brønsted acids. Other sources which may provide suitable anions include the optionally halogenated tetraphenyl borate derivatives, e.g. perfluorotetraphenyl borate. Additionally, zero-valent palladium complexes particularly those with labile ligands, e.g., triphenylphosphine or alkenes such as dibenzylideneacetone or styrene may be used.

As used herein, the term "activating anion" refers to a compound comprising an anion or anions also present in the reaction mixture, either as a portion of the transition metal compound (i.e., as its anion) or as an added species, tend to donate the anion in to the transition metal (e.g., Ru or Pd) in a coordinating fashion or it may be present in solution in a non-coordinating manner; accordingly, the catalyst system above refers to the "reaction product of" (a) and (b) to relate to both circumstances. Such activating anions are necessary for the overall operability of the catalyst system. Such anions may be introduced into the solution as an acid having a pKa of less than 4 or as a salt containing a cation that does not interfere with the reaction. Such salts may include metal salts, e.g. LiCl, NaCl, KCl, LiBr, NaBr, KBr, LiI, NaI, KBr, and the like. Such salts may also include large organic moieties such as tetra alkyl ammonium salts such as tetra($C_1$-$C_6$ alkyl)ammonium salts. Acids suitable for this reaction include hydrochloric acid, sulfuric acid, phosphoric acid, nitric acid, aryl sulfonic acids, and the like. In one embodiment, the activating anion source is para-tolyl sulfonic acid.

In certain embodiments, the catalyst system comprises a phosphorous compound capable of forming a bidentate phosphorus ligand. Phosphines of the formula $R^1R^2R^3P$ may be used. In practice of the invention, $R^1$, $R^2$, and $R^3$ are independently any alkyl or aryl group, containing 1 to 20 carbons. The aryl group moieties may also be heteroaryl groups. The alkyl and aryl/heteroaryl group moieties may optionally be substituted with heteroatom containing groups such as hydroxyl, ether, amine, thioether, carboxylate esters, chloride, or fluoride provided the substituents do not interfere with the catalytic reaction by acting as a poison or inhibitor. Examples of such substituent groups include groups chosen from $C_1$-$C_6$ alkyl, $C_1$-$C_6$ alkoxy, —CN, —NO$_2$, $C_1$-$C_6$ alkoxycarbonyl, $C_1$-$C_6$ alkanoyloxy, $C_1$-$C_6$ alkylsulfonyl, hydroxyl, carboxyl, and halogen. In one embodiment of the invention, triphenyl phosphine is utilized as a further component of the catalyst system.

In certain embodiments, the phosphorus containing compound is of the formula $R^1R^2P^1$—X—$PR^3R^4$ in which $R^1$, $R^2$, $R^3$, and $R^4$ are any alkyl, aryl, or heteroaryl groups containing 1 to 20 carbon atoms. The divalent linking group —X—, may be any divalent alkyl or aryl group containing 1 to 20 carbon atoms and optionally substituted in a like manner. Such phosphines coordinate to the transition metal, for example Pd atom, in a bidentate manner.

As used herein, the term "aryl" includes phenyl and napthyl and such groups substituted with one to three groups chosen from $C_1$-$C_6$ alkyl, $C_1$-$C_6$ alkoxy, —CN, —NO$_2$, $C_1$-$C_6$ alkoxycarbonyl, $C_1$-$C_6$ alkanoyloxy, $C_1$-$C_6$ alkylsulfonyl, hydroxyl, carboxyl, and halogen. The term "heteroaryl" includes 5 or 6-membered heterocyclic aryl rings containing one oxygen atom, and/or one sulfur atom, and up to three nitrogen atoms, said heterocyclic aryl ring optionally fused to one or two phenyl rings. Examples of such systems include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo-[1,5-b]pyridazinyl and purinyl, benzoxazolyl, benzothiazolyl, benzimidazolyl, indolyl and the like; such groups are optionally substituted with one to three groups selected from $C_1$-$C_6$-alkyl, $C_1$-$C_6$-alkoxy, —CN, —NO$_2$, $C_1$-$C_6$-alkoxycarbonyl, $C_1$-$C_6$-alkanoyloxy, $C_1$-$C_6$-alkylsulfonyl, and halogen groups.

Other examples of suitable phosphine ligands include those described in U.S. Pat. Nos. 4,148,830; 4,593,127; 4,769,498; and 4,717,775, incorporated herein by reference.

The catalyst system, including palladium or ruthenium source, optional phosphorus containing ligand, and activating anion component should be chosen such that the resultant system is not adversely affected by the presence of water.

The reaction may be conducted at temperatures from about 50° C. to 200° C. In one embodiment, the reaction is conducted between about 75° C. and about 165° C. In one embodiment, the reaction is conducted at a pressure of least about 1375 kPa. In other embodiments, the reaction is conducted at pressures from about 1375 kPa to about 4100 kPa or from about 2000 kPa to about 3450 kPa.

The reaction can be conducted in a solvent such that the homogeneous catalyst system, a $C_1$-$C_6$ alkanol, e.g., methanol, and gas mixture are all dissolved in that solvent. The solvent can be any non-reacting material such as a hydrocarbon, ester, ether, or amine. Further examples of such solvents include one or more aprotic solvents such as ethers, e.g. diethyl ether, dimethyl ether of diethylene glycol, anisole and diphenyl ether, aromatic compounds, including halo variants of such compounds, e.g. benzene, toluene, ethyl benzene, o-xylene, m-xylene, p-xylene, chlorobenzene, odichlorobenzene, mdichlorobenzene, and p-dichlorobenzene; alkanes, including halo variants of such compounds, e.g., hexane, heptane, 2,2,3-trimethylpentane, methylene chloride and carbon tetrachloride; nitriles, e.g., benzonitrile and acetonitrile; esters, e.g., methyl benzoate, methyl acetate, methyl propionate and dimethyl phthalate; sulfones, e.g., diethyl sulfone and tetrahydrothiophene 1,1-dioxide; carboxylic acids, e.g., propionic acid. In one embodiment, a solvent is used as a solvent a compound which takes part in the reaction either as a reactant or a product, to minimize the number of different compounds present in the liquid phase to facilitate separation of the mixture. In one embodiment, ethylene is carbonylated in the presence of carbon monoxide in the presence of methanol to form methyl propionate, utilizing methyl propionate as solvent. In another embodiment, the solvent is N-methyl-2-pyrrolidinone.

The solvent can allow for efficient recycle of the catalyst if it is higher boiling than the other components in the reaction mixture. The solvent can also be chosen such that it improves solubility of the gases in the reaction mixture.

The reaction may be conducted utilizing any molar combination of CO and ethylene. In one embodiment, the reaction is conducted where the partial pressure of CO is twice that of ethylene. In another embodiment, the reaction is conducted such that the partial pressure of ethylene is twice that of CO. In a certain embodiment, the partial pressure of ethylene is equal to that of CO.

The hydrolysis portion of the one pot propionic acid synthesis is carried out by adding a measured amount of water to the reactor at the same time as the methoxycarbonylation components. The amount of water can vary but should be enough to exceed about 1 molar equivalent of the methanol added to the reactor and thus exceed about 1 molar equivalent of the theoretical methyl propionate that may be formed. In certain embodiments, the amount of water present in the reactor greatly exceeds one molar equivalent of the methanol such that the equilibrium of the hydrolysis reaction lies far to the right (Le Chatlier's Principle). In other embodiments, the amount of water lies between 3 molar equivalents and 8 molar equivalents relative to the methanol present in the reactor.

The hydrolysis is carried out in the same reactor at the same temperature and pressure as the methoxycarbonylation reaction. Thus, the reaction can be referred to as a "one-pot" synthesis of propionic acid.

In an embodiment of the invention, referring to the FIGURE, stream 6 containing fresh methanol feed, stream 7 containing fresh water feed, and stream 8 containing the homogeneous catalyst system and an optional solvent are fed into reactor vessel 1. Stream 9 containing CO and stream 10 containing ethylene are also fed into vessel 1. The crude reaction mixture, stream 11, containing propionic acid product, methyl propionate intermediate, and unreacted methanol, water, ethylene, and CO, along with catalyst and solvent, is fed into vessel 2 which acts as a liquid/vapor separation vessel. Unreacted ethylene and CO are separated, compressed, and returned to vessel 1 via stream 12. Crude liquids are fed into distillation column 3 via stream 13. In distillation column 3, methanol and water are separated and recovered overhead and are recycled to vessel 1 via stream 14. Stream 15, containing methyl propionate, propionic acid, catalyst, and solvent is fed to distillation column 4. Distillation column 4 separates unreacted methyl propionate overhead and returns in to vessel 1 via stream 16 which can, if desired, mix with stream 14. Stream 17 containing propionic acid, catalyst, and solvent, is fed to distillation column 5. Distillation column 5 separates product propionic acid overhead (stream 18). Stream 19 exits the bottom of distillation column 5 containing recovered catalyst and solvent. Stream 19 recycles the catalyst and solvent back to reactor vessel 1. Any necessary fresh catalyst, anion activator, solvent, methanol, water, and ethylene can then be recharged into the reactor vessel 1 so as to provide a continuous reaction mode or regime. Accordingly, in a further embodiment, the invention provides the above process, conducted in a continuous mode.

This invention can be further illustrated by the following examples of preferred embodiments thereof, although it will be understood that these examples are included merely for purposes of illustration and are not intended to limit the scope of the invention unless otherwise specifically indicated.

Examples

Methoxycarbonylation to Methyl Propionate

Example A. A 100 mL Hastelloy autoclave was charged with 23.6 g (30 mL, 736 mmol) of methanol. 0.118 g of Pd(II) acetate (0.526 mmol) and 1.00 g (2.53 mmol) of 1,2-bis(di-tert-butylphosphinomethyl) benzene was added. The autoclave was sealed and placed in an electric heating apparatus and attached to an overhead stirring motor. The autoclave was heated to 80° C. and stirred at 500 rpm. Upon reaching temperature, ethylene was introduced to the reactor at 24 standard cubic centimeters per minute (SCCM) and carbon monoxide (CO) introduced at 12 SCCM until a pressure of 2068 kPa was reached. Constant pressure was maintained by gas flow for 4 h. After 4 h, the reactor was cooled, vented, and the contents analyzed by gas chromatography (GC). The reactor was found to contain 24.5 g methyl propionate (278 mmol). This corresponded to a turnover number (TON) of 528 (mol methyl propionate/mol Pd) and a turnover frequency (TOF) of 132 $h^{-1}$.

Example B. A 100 mL Hastelloy autoclave was charged with 23.6 g (30 mL, 736 mmol) of methanol. 0.184 g of Pd(II) acetate (0.820 mmol) and 1.81 g (3.28 mmol) of 2,2-Bis(diphenyphosphinomethyl) biphenyl phosphine was added. The autoclave was sealed and placed in an electric heating apparatus and attached to an overhead stirring motor. The autoclave was heated to 80° C. and stirred at 500 rpm. Upon reaching temperature, ethylene was introduced to the reactor at 24 SCCM and carbon monoxide (CO) was introduced at 12 SCCM until a pressure of 1723 kPa was reached. Constant pressure was maintained by gas flow for 4 h. After 4 h, the reactor was cooled, vented, and the contents analyzed by GC. The reactor was found to contain 25.8 g of methyl propionate (293 mmol). This corresponded to a TON of 358 (mol methyl propionate/mol Pd) and a TOF of 89 $h^{-1}$.

Example C. A 100 mL Hastelloy autoclave was charged with 23.7 g (30 mL, 742 mmol) of methanol. 0.184 g of Pd(II) acetate (0.526 mmol), 0.86 g (3.27 mmol) of triphenyl phosphine, and 0.312 g (1.64 mmol) of para-tolyl sulfonic acid monohydrate are added. The autoclave was sealed and placed in an electric heating apparatus and attached to an overhead stirring motor. The autoclave was heated to 80° C. and stirred at 500 rpm. Upon reaching temperature, ethylene was introduced to the reactor at 24 SCCM and carbon monoxide (CO) introduced at 12 SCCM until a pressure of 2068 kPa was reached. Constant pressure was maintained by gas flow for 4 h. After 4 h, the reactor was cooled, vented, and the contents analyzed by GC. The reactor was found to contain 11.6 g of methyl propionate (131 mmol). This corresponded to a TON of 160 (mol methyl propionate/mol Pd) and a TOF of 40 h-1.

Example D. A 100 mL Hastelloy autoclave was charged with 7.71 g (10 mL, 241 mmol) of methanol. 0.064 g of $Ru_3(CO)_{12}$ (0.100 mmol) and 0.212 g of LiCl (5.00 mmol) are added. 10 mL of N-methyl-2-pyrrolidinone (NMP) was added. The autoclave was sealed and placed in an electric heating apparatus and attached to an overhead stirring motor. The autoclave was heated to 160° C. and stirred at 500 rpm. Upon reaching temperature, ethylene was introduced to the reactor at 24 SCCM and carbon monoxide (CO) was introduced at 12 SCCM until a pressure of 3447 kPa was reached. Constant pressure was maintained by gas flow for 4 h. After 4 h, the reactor was cooled, vented, and the contents analyzed by GC. The reactor was found to contain 8.9 g of methyl propionate (101 mmol). This corresponded to a TON of 331 (mol methyl propionate/mol Ru) and a TOF of 55 h-1.

In situ Hydrolysis of Methyl Propionate to Propionic Acid

Example 1. A 100 mL Hastelloy autoclave was charged with 7.1 g (10 mL, 222 mmol) of methanol and 29.6 (30 mL, 1644 mmol) of water. 0.092 g of Pd(II) acetate (0.410 mmol), 0.430 g (1.639 mmol) of triphenyl phosphine, and 0.312 g (1.64 mmol) of para-tolyl sulfonic acid monohydrate were added. The autoclave was sealed and placed in an electric heating apparatus and attached to an overhead stirring motor. The autoclave was heated to 80° C. and stirred at 500 rpm. Upon reaching temperature, ethylene was introduced to the reactor at 24 SCCM and carbon monoxide (CO) was introduced at 12 SCCM until a pressure of 2068 kPa was reached. Constant pressure was maintained by gas flow for 4 h. After 4 h, the reactor was opened and analyzed by GC. The reactor contents contained 0.39 g of methyl propionate and 0.61 g of propionic acid. This corresponded to 6% conversion of methanol and a TON of 20 mol propionic acid/mol Pd.

Example 2—Example 2 was repeated but the reactor was charged with 15.2 g (20 mL, 475 mmol) of methanol and 19.2 (20 mL, 1067 mmol) of water. After 4 h, the reactor was found to contain 2.84 g of methyl propionate and 1.38 g of propionic acid. This corresponded to a methanol conversion of 10.3% and a TON of 46 mol propionic acid/mol Pd.

Example 3. Experiment B was repeated except the reactor was charged with 20 mL methanol and 20 mL water. After 4 h, the reactor was cooled and sampled. The reaction mixture was found to contain 10.6 g of methyl propionate and 4.19 g of propionic acid. This corresponded to 42.3% conversion of methanol and a TON of 68.9 mol propionic acid/mol Pd.

Example 4. Example 3 was repeated but the reactor was charged with 10 mL methanol and 30 mL water. After 4 h the reactor was found to contain 0.55 g of methyl propionate and 0.86 g of propionic acid. This corresponded to a methanol conversion of 7.1% and a TON of 14 mol propionic acid/mol Pd.

Example 5. Example D was repeated except the reactor was charged with 10 mL methanol and 20 mL water. In addition, 0.048 g (0.253 mmol) of para-tolyl sulfonic acid monohydrate was added to the reactor to promote ester hydrolysis. After 4 h, the reactor was cooled, vented, and its contents analyzed by GC. The reactor was found to contain 2.92 g of methyl propionate and 2.02 g of propionic acid. This corresponded to 27.2% conversion of methanol and a TON of 89 mol propionic acid/mol Ru.

The invention has been described in detail with particular reference to certain embodiments thereof, but it will be understood that variations and modifications can be effected within the spirit and scope of the invention.

The invention claimed is:

1. A one-pot process for preparing propionic acid, which comprises:

treating ethylene with a $C_1$-$C_6$ alkanol, water, and carbon monoxide in the presence of a catalyst system comprising the reaction product of:

(a) a Group 8 to 10 transition metal compound; and (b) an activating anion;

at a temperature of about 50° C. to about 200° C., and a pressure of at least 1375 kPa; provided that when said transition metal compound is palladium, the catalyst system further comprises at least one phosphorous compound; wherein the Group 8 to 10 transition metal compound is chosen from compounds comprising palladium and ruthenium; and wherein the activating anion is provided by the addition of p-tolyl sulfonic acid.

2. The process of claim 1, wherein the Group 8 to 10 transition metal compound is chosen from compounds comprising at least one metal chosen from iron, ruthenium, osmium, cobalt, nickel, palladium, rhodium, and platinum.

3. The process of claim 1, wherein the activating anion is provided by addition of salts and acids chosen from alkali metal halides, alkali metal sulfates, alkali metal phosphates, alkali metal nitrates, alkali metal p-tolylsulfonates, HCl, $H_2SO_4$, $HNO_3$, $H_3PO_4$, and aryl sulfonic acids.

4. The process of claim 1, wherein the $C_1$-$C_6$ alkanol is methanol.

5. The process of claim 1, wherein the pressure is less than 4100 kPa.

6. The process of claim 1, wherein the pressure is 2000 kPa to 3450 kPa.

7. The process of claim 1, wherein the temperature is 75° C. to 165° C.

8. The process of claim 1, wherein the Group 8 to 10 transition metal compound is Pd (II) acetate.

9. The process of claim 1, wherein the Group 8 to 10 transition metal compound is $Ru_3(CO)_{12}$.

10. The process of claim 1, wherein the catalyst system further comprises:

(c) a phosphorous compound capable of forming a bidentate ligand with the Group 8 to 10 transition metal.

11. The process of claim 10, wherein the phosphorous compound is a phosphine having the formula $R^1R^2R^3P$, wherein $R^1$, $R^2$, and $R^3$ are independently chosen from alkyl, aryl, or heteroaryl groups, containing 1 to 20 carbons atoms.

12. The process of claim 1, wherein the phosphorous compound is from chosen 1,2-bis(di-tert-butylphosphinomethyl) benzene; 2,2-Bis(diphenyphosphinomethyl) biphenyl phosphine; and triphenyl phosphine.

13. The process of claim 1, wherein the process is conducted in continuous mode.

14. A one-pot process for preparing propionic acid, which comprises:

treating ethylene with a $C_1$-$C_6$ alkanol, water, and carbon monoxide in the presence of a catalyst system comprising the reaction product of:

(a) a Group 8 to 10 transition metal compound, (b) an activating anion, and (c) a phosphorous compound capable of forming a bidentate ligand with the Group 8 to 10 transition metal compound, at a temperature of about 50° C. to about 200° C., and a pressure of at least 1375 kPa; provided that when said transition metal compound is palladium, the catalyst system further comprises at least one phosphorous compound; wherein the Group 8 to 10 transition metal compound is chosen from compounds comprising palladium and ruthenium; and wherein the activating anion is provided by the addition of p-tolyl sulfonic acid.

15. The process of claim 14, wherein the $C_1$-$C_6$ alkanol is methanol, wherein the Group 8 to 10 transition metal compound is chosen from compounds comprising palladium and ruthenium, and wherein the activating anion is provided by the addition of p-tolyl sulfonic acid.

16. The process of claim 14, wherein the phosphorous compound is chosen from 1,2-bis(di-tert-butylphosphinomethyl) benzene; 2,2-Bis(diphenyphosphinomethyl) biphenyl phosphine; and triphenyl phosphine.

* * * * *